(12) United States Patent
Quillin et al.

(10) Patent No.: US 7,878,793 B2
(45) Date of Patent: Feb. 1, 2011

(54) APPARATUS AND METHOD FOR RE-COLORING, RECOVERING, REPAIRING AND REFORMULATING COSMETIC LIP PRODUCTS

(75) Inventors: Jill Quillin, Knoxville, TN (US); Jack S. Peterson, Knoxville, TN (US)

(73) Assignee: Divine Innovations, LLC, Knoxville, TN (US)

( * ) Notice: Subject to any disclaimer, the term of this patent is extended or adjusted under 35 U.S.C. 154(b) by 58 days.

(21) Appl. No.: 12/358,963

(22) Filed: Jan. 23, 2009

(65) Prior Publication Data

US 2009/0189311 A1 Jul. 30, 2009

Related U.S. Application Data

(60) Provisional application No. 61/023,157, filed on Jan. 24, 2008.

(51) Int. Cl.
*B29C 39/04* (2006.01)
*B29C 39/22* (2006.01)

(52) U.S. Cl. ..................... 425/450.1; 425/215

(58) Field of Classification Search ................ 264/300, 264/310, 334; 425/215, 450.1
See application file for complete search history.

(56) References Cited

U.S. PATENT DOCUMENTS 3,493,309 A * 2/1970 Grisel ................ 401/78
3,891,179 A * 6/1975 Berman ............... 249/134
4,188,009 A 2/1980 Gillispie
5,780,018 A 7/1998 Collins et al.
5,971,351 A 10/1999 Swaab
6,033,606 A 3/2000 Garza
6,050,540 A 4/2000 O'Reilly
6,402,120 B1 * 6/2002 Swaab ................ 249/117
2003/0107152 A1 6/2003 Cziraky

* cited by examiner

*Primary Examiner*—Kat Wyrozebski
*Assistant Examiner*—Robert J Grun
(74) *Attorney, Agent, or Firm*—Luedeka, Neely & Graham, P.C.

(57) ABSTRACT

A lip product remixing kit contains tools that provide for recovering unused cosmetic lip material from applicator containers, and remixing and remolding the materials to form reconstituted cosmetic lip products. Using the kit, one may re-color their lip product by combining two or more lip products so as to customize the overall appearance (color and shape) and consistency of the product as desired by the user. The kit also provides tools needed to recover the unused lipstick material in the base of an applicator tube and to re-mold the material into a new stick that may be inserted into a new or used applicator tube. Other uses for the kit are to repair a broken lipstick and reformulate a lipstick into lip gloss. In a preferred embodiment, the kit includes spatulas, mixing/measuring containers, storage containers, lip product applicator tubes with stickers, instructions, a tube of clear gloss and a mold for forming reconstituted sticks of lipstick.

8 Claims, 6 Drawing Sheets

APPARATUS AND METHOD FOR RE-COLORING, RECOVERING, REPAIRING AND REFORMULATING COSMETIC LIP PRODUCTS

This application claims priority to U.S. provisional patent application Ser. No. 61/023,157 filed Jan. 24, 2008, entitled Apparatus and Method for Re-Coloring, Recovering, Repairing and Reformulating Cosmetic Lip Products, the entire contents of which are incorporated herein by reference.

FIELD

This invention relates to the field of cosmetics. More particularly the invention relates to an apparatus and method for re-coloring, recovering, repairing and reformulating lipstick and lip gloss.

BACKGROUND

Retail cosmetic lip products, such as lipstick and lip gloss, are relatively expensive and most are non-returnable if a purchaser becomes dissatisfied with the product once the product has left the store. There are many reasons why a purchaser may not be satisfied with any particular lip product. For example, the product may have broken or not have the desired color or texture, the product may cause lip dryness or other physiological problems, or the purchaser may dislike the flavor of the product. Since unsatisfactory lip products cannot be returned to the store, these products will probably go unused and will be of no value to the purchaser.

Some consumers may attempt to re-color an unsatisfactory lip product into something useable by applying one lip product on their lips over another lip product to attain a desired color or texture. Such a remedy is not always convenient or effective. Therefore, what is needed is a means to re-color unsatisfactory lip products into something useable.

Another problem with lipstick products is the waste involved. With a lipstick tube, which is the standard lipstick packaging scheme, about one-third of the lipstick product in the base of the tube is inaccessible and therefore unusable. Thus, what is also needed is a means for recovering the lipstick in the base of the tube so that it may be made usable.

Another problem with lipstick products is their sensitivity to heat or pressure. If a lipstick product is broken, a means for repairing the lipstick is necessary so that it may be made usable.

Another option for lipstick is to be reformulated into lip gloss. If a consumer has a supply of lipstick, but is only wearing lip gloss, they need a means for reformulating the lipstick to turn it into lip gloss so that it becomes usable.

SUMMARY

The above and other needs are met by a lip product recovering, re-coloring, repairing and reformulating kit and method. The kit contains tools that provide for recovering unused lip cosmetic material from applicator containers, and remixing and remolding the materials to form reconstituted lip cosmetic products. Using the kit, one may also recolor lipstick by combining two or more lip products so as to customize the overall appearance (color and shape) and consistency of the product as desired by the user. The kit also provides the tools needed to repair a broken lipstick and to re-mold the material into a new bullet-shaped stick that may be inserted into a new or previously used applicator tube. The kit also includes the tools necessary to reformulate lipstick into lip gloss. In a preferred embodiment, the kit includes spatulas, measuring/mixing containers, storage containers, lip product containers with stickers, a mold for forming reconstituted sticks of lipstick, instructions and cosmetic bag.

In another embodiment, the invention provides a method for molding a stick of lip product. The method of this embodiment includes steps of:
(a) engaging a first half of a lower mold section with a second half of the lower mold section, thereby forming a lower mold cavity having a substantially cylindrical upper portion disposed along a central mold axis;
(b) inserting the lower mold section into an upper mold section, wherein the upper mold section includes a substantially cylindrical upper mold cavity disposed along the central mold axis;
(c) pressing the upper mold section against the lower mold section, thereby abuttingly engaging the upper mold cavity with the upper portion of the lower mold cavity, thereby forming a composite mold cavity;
(d) substantially filling the composite mold cavity with a molten lip product;
(e) allowing the molten lip product to cool and solidify within the composite mold cavity to form the stick of lip product;
(f) rotating the upper mold section about the central mold axis with respect to the lower mold section, the rotation causing the upper mold cavity to release from the stick of lip product while simultaneously causing the upper mold section to move axially away from the lower mold section in the direction of the central mold axis;
(g) separating the upper mold section from the lower mold section, thereby exposing an upper portion of the stick of lip product that was formed in the upper mold cavity; and
(h) removing the stick of lip product from the lower mold section.

In yet another embodiment, the invention provides a mold for forming a stick of lip product. The mold of this embodiment includes a lower mold section, an upper mold section, and means for causing the upper mold section to separate from the lower mold section due to rotation of the upper mold section about a central mold axis with respect to the lower mold section. The lower mold section has a lower mold cavity, at least an upper portion of which is substantially cylindrical and disposed along the central mold axis. The lower mold section includes a first lower mold portion in which a first half of the lower mold cavity is disposed, and a second lower mold portion in which a second half of the lower mold cavity is disposed. The upper mold section has a substantially cylindrical upper mold cavity which engages the upper portion of the lower mold cavity to form a composite mold cavity when the upper mold section is engaged with the lower mold section.

In one preferred embodiment, the lower mold section includes a base section with an upper surface having upwardly extending ramp members disposed thereon. The upper mold section of this embodiment includes downwardly extending tabs that are in rotational alignment with the ramp members of the lower mold section when the upper mold section is engaged with the lower mold section. The means for causing the upper mold section to separate from the lower mold section comprises the ramp members in sliding engagement with the tabs as the upper mold section is rotated about the central mold axis with respect to the lower mold section.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
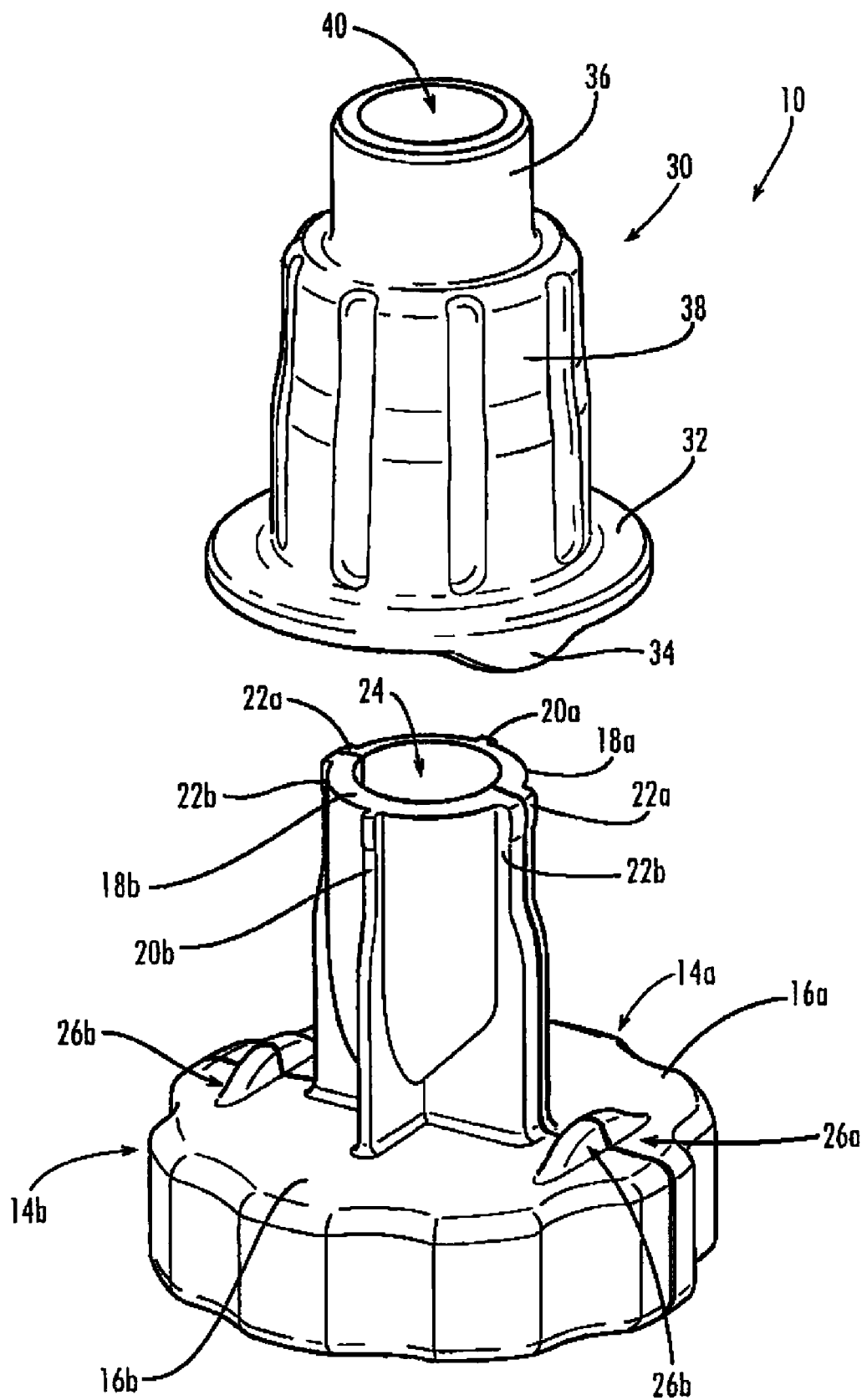
FIG. 1 depicts a perspective view of a partially assembled lipstick mold according to an embodiment of the invention.
Figure 2:
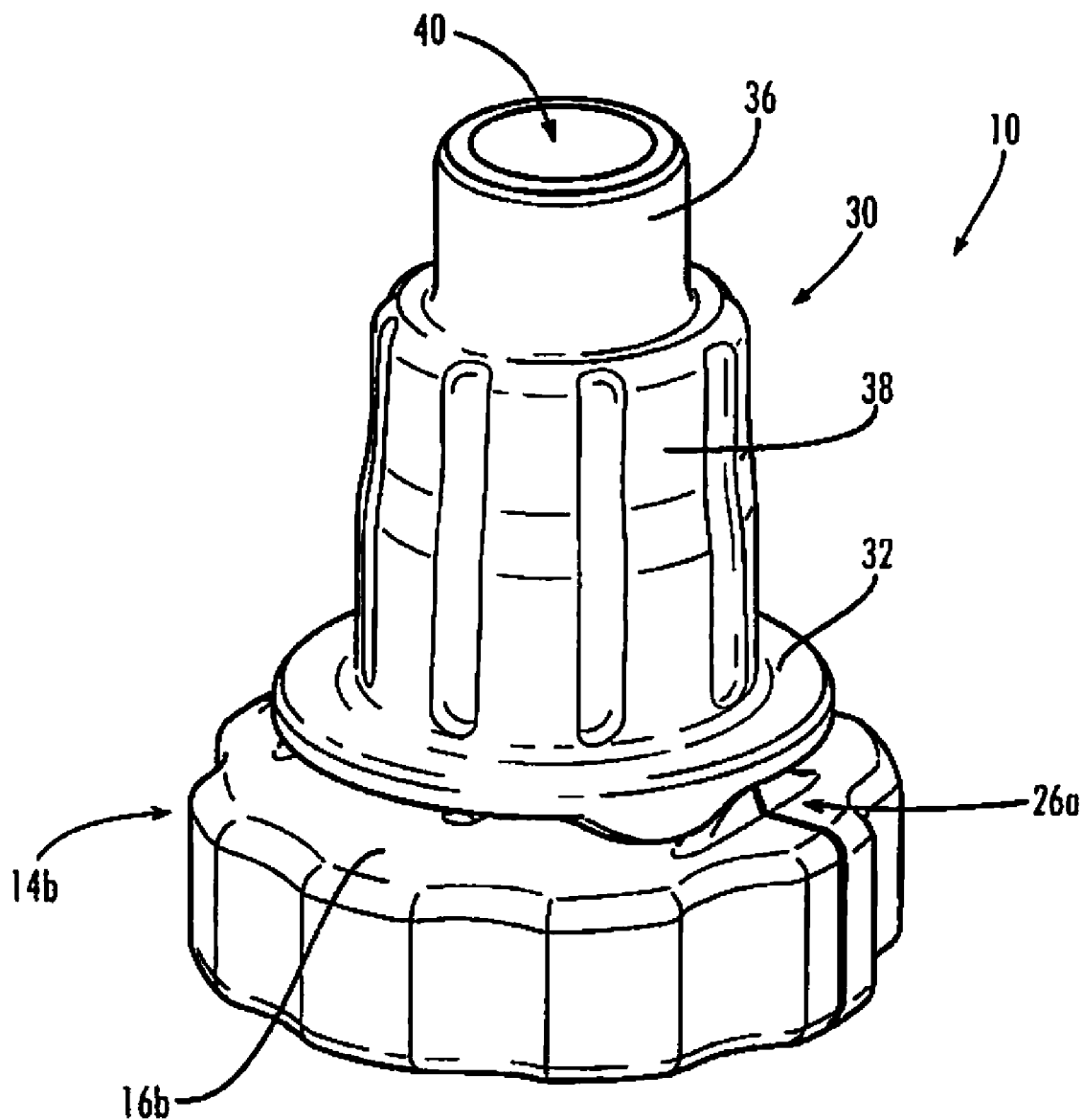
FIG. 2 depicts a perspective view of a completely assembled lipstick mold according to an embodiment of the invention.
Figure 3:
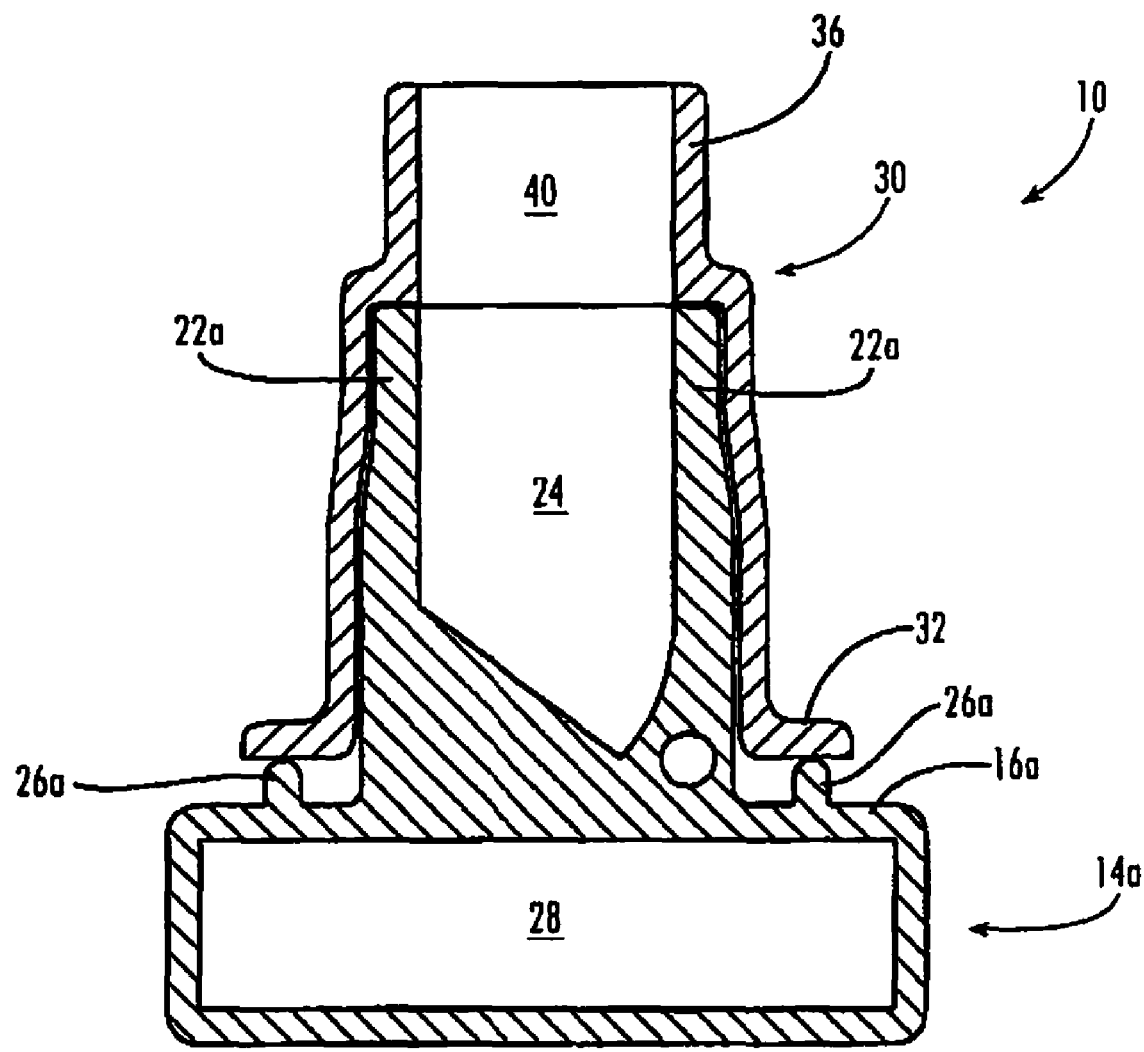
FIG. 3 depicts a cross-section view of a completely assembled lipstick mold according to an embodiment of the invention.

As shown in FIGS. 1-3, a preferred embodiment of a lipstick mold 10 includes two main components: an upper mold section 30 and a lower mold section 12. The lower mold section 12 comprises lower mold half 14a and lower mold half 14b which are preferably complementary in structure. The upper mold section 30 and lower mold halves 14a-14b are preferably molded parts formed of thermoplastic, such as by an injection molding process. In a most preferred embodiment, the upper mold section 30 and lower mold halves 14a-14b are formed from an acetal homopolymer, such as Delrin® which is manufactured by Ensinger-Hyde. It has been determined that the acetal material is advantageous in providing a clean release between the mold and the lipstick material. In alternative embodiments, the upper mold section 30 and lower mold halves 14a-14b may be formed of metal, ceramic or wood.

When the lower mold halves 14a-14b are joined together as shown in FIG. 1, they form a lower cavity 24 bounded by lower mold walls 18a and 18b. The lower mold walls 18a-18b are supported by ribs 20a and 22a of the lower mold half 14a and ribs 20b and 22b of the lower mold half 14b. The ribs 20a-20b and 22a-22b are supported on an upper surface of base sections 16a-16b. As shown in FIG. 3, the base sections 16a-16b are preferably hollow, having a cavity 28 therein. On the upper surface of the base sections 16a-16b are ramp members 26a-26b. These ramp members 26a-26b are disposed on opposing sides of the base sections 16a-16b (about 180 degrees apart) and are spaced apart by a distance of about 1.25 inches.

As shown in FIG. 3, the bottom of the lower cavity 24 is preferably somewhat pointed or bullet-shaped and includes a flattened portion to one side. In this configuration, the lower cavity 24 forms a lipstick shape which is well-known and accepted in the industry. The upper portion of the lower cavity 24 is substantially cylindrical, having a diameter of about 0.5 inch in a preferred embodiment.

The upper mold section 30 comprises a contoured tube, having an upper cylindrical section 36, a lower tapered section 38 and a base flange 32. Within the upper section 36 is a generally cylindrical cavity 40, having a diameter of about 0.5 inch in a preferred embodiment. The lower tapered section 38 has an inner surface that generally follows the contour of the outer edges of the ribs 20a-20b and 22a-22b of the lower mold halves 16a-6b. As shown in FIG. 3, when the lower mold halves 16a-16b are inserted into the upper mold section 30, the outer edges of the ribs 20a-20b and 22a-22b engage the inner surface of the upper mold section 30 so that the upper cavity 40 aligns with the lower cavity 24. In the preferred embodiment, the outer edges of the ribs 20a-20b and 22a-22b include features (such as bumps) that snap into corresponding features (such as grooves) on the inner surface of the upper mold section 30 when the upper mold section 30 is pressed down onto the lower mold halves 16a-16b.

Extending downward from the bottom surface of the base flange 32 are a pair of tabs 34. These tabs 34 are disposed on opposing sides of the base flange 32 (about 180 degrees apart) and are spaced apart by a distance which is substantially equivalent to the distance between the opposing ramp members 26a-26b on the upper surface of the base sections 16a-16b of the lower mold halves 14a-14b. When the lower mold halves 16a-16b are inserted into the upper mold section 30, the tabs 34 may engage the upper surface of the base sections 16a-16b or they may engage the ramp members 26a-26b, depending on the axial rotational relationship between the upper mold section 30 and the lower mold halves 14a-14b.

When the upper mold section 30 is rotated about the central axis of the mold into a position where the tabs 34 are disposed between the opposing ramp members 26a-26b, the lower surface of the flange 32 will contact the ramp members 26a-26b, and the bottom edge of the upper section 36 will be flush against the top edges of the lower mold walls 18a-18b. This is referred to as the mold-engaged position, wherein the upper cavity 40 and lower cavity 24 form one continuous cylindrical cavity for molding a stick of lipstick.

As the upper mold section 30 is rotated about the central axis of the mold away from the mold-engaged position, the tabs 34 eventually engage and ride up onto the ramp members 26a-26b. When this occurs, the lower surface of the flange 32 is forced upward and away from the base sections 16a-16b of the lower mold halves 14a-14b. At the same time, the bottom edge of the upper section 36 disengages from the top edges of the lower mold walls 18a-18b. This is referred to as the mold-break position, wherein the upper cavity 40 has been rotated upward and away from the lower cavity 24. The rotation of the upper mold section 30 as it moves into the mold-break position provides for a clean release of the inner surfaces of the mold cavity 40 from the molded lipstick material.

Thus, in a preferred embodiment, the ramp members 26a-26b and tabs 34 comprise means for disengaging the upper mold section 30 from the lower mold halves 16a-16b when the upper mold section 30 is rotated in relation to the lower mold halves 16a-16b. In other embodiments, the means for disengaging the upper mold section 30 from the lower mold halves 16a-16b comprise threads formed on the outer surfaces of the lower mold walls 18a and 18b and matching threads on the inner surface of the lower tapered section 38 of the upper mold section 30.

Figure 4:
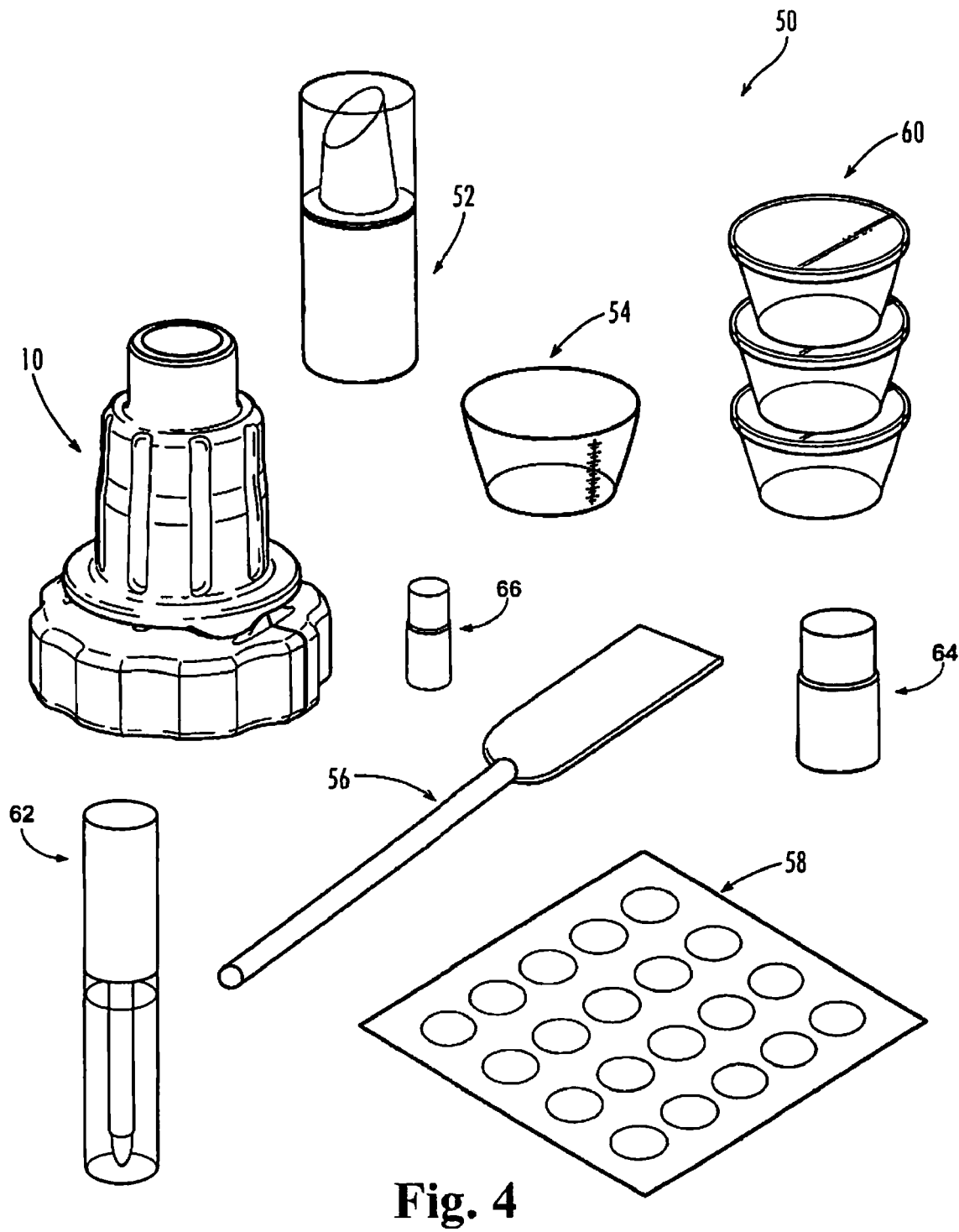
FIG. 4 depicts a kit of materials and components used in re-coloring, repairing, recovering and reformulating lipstick according to an embodiment of the invention.

FIG. 4 depicts a preferred embodiment of a kit 50 for re-coloring, recovering, repairing and reformulating cosmetic lip products. The kit 50 includes the lipstick mold 10, mixing/measuring containers 54 in which to mix and heat the lip product materials, spatulas 56 for retrieving and mixing lip product materials, lipstick applicator tubes 52, lip gloss containers 64, a tube of clear lip gloss 62, label stickers 58 for attaching to the lipstick tubes and lip gloss containers, and stackable storage containers 60 for storing unused lipstick and lip gloss material. The mixing containers 54 may be formed from any number of materials that are compatible with use in a microwave oven, such as plastic, paper or ceramic. The spatulas 56 may also be formed from various materials, such as plastic, wood or metal. The storage containers 60 are preferably of the plastic "screw top" type. The kit 50 may also include a container 66 of mold release agent.

Figure 5:
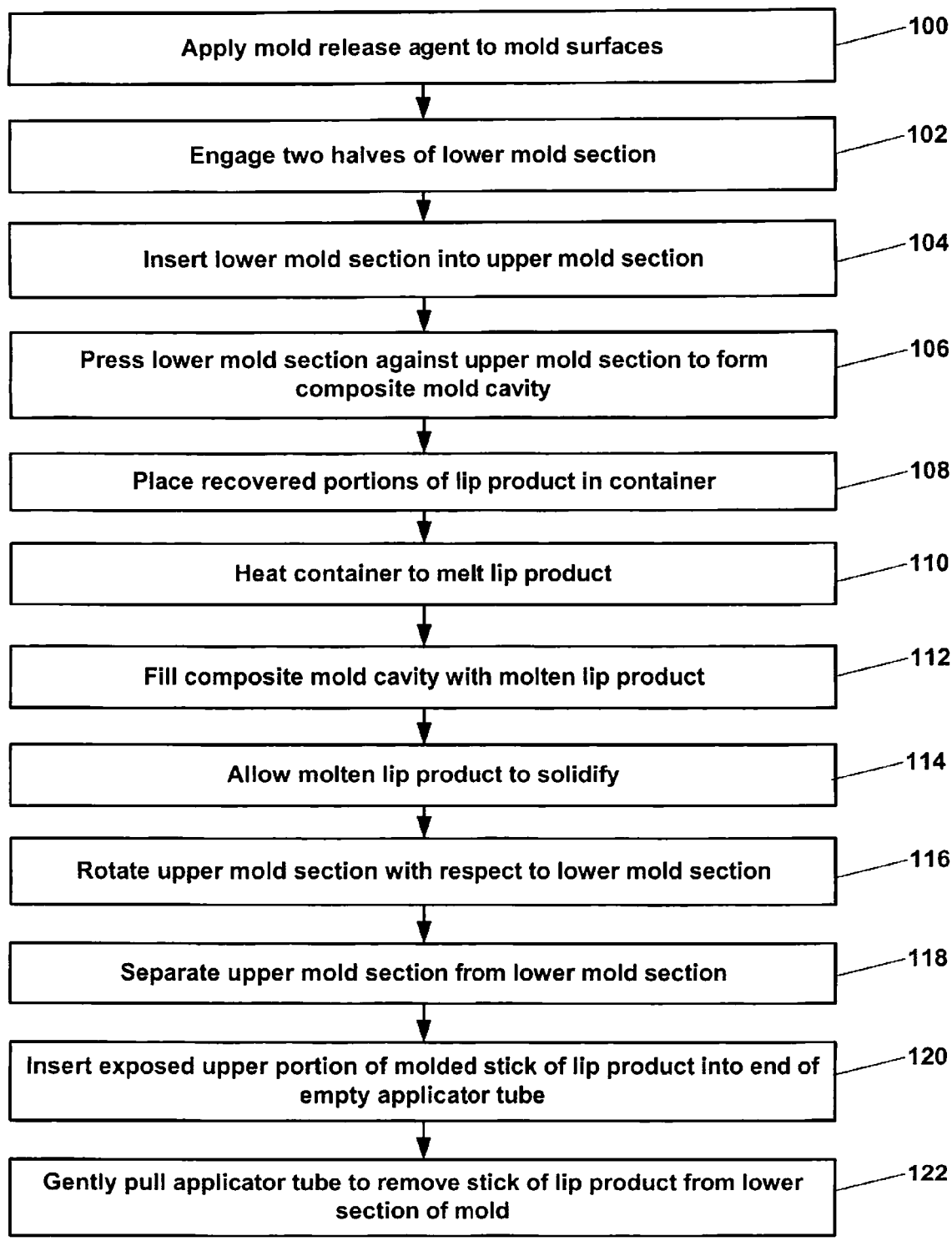
FIG. 5 depicts steps of a method for molding a stick of lip product according to an embodiment of the invention.

Procedure for Using the Kit 50 to Re-Color, Recover, Repair and Reformulate Lip Products The following procedure is described with reference to the steps depicted in FIG. 5. First, a mold release agent is preferably applied to the inside surface of each of the lower mold halves 14a-14b and on the inside surface of the upper cylindrical section 36 of the upper mold section 30 (step 100 of FIG. 5). In a preferred embodiment, the mold release agent is a nonstick cooking spray which is applied to a paper and spread evenly over the inside surfaces of the mold pieces. The mold 10 is then assembled by lining up the two lower mold halves 14a-14b (step 102) and placing the upper mold section 30 onto the lower mold halves 14a-14b (step 104). Downward pressure should be applied to the upper mold section 30 until it snaps into place, indicating it is fully engaged with the lower mold halves 14a-14b (step 106).

Using the spatula 56, lipstick material is added to a mixing container 54 (step 108). The lipstick material may have been recovered from the bottom of a used applicator tube. Materials of different colors may be added to mix to re-color lip product. Also, a broken lipstick may be added to the mixing container to repair and reuse. Lipstick and lip gloss may be combined to reformulate the lip products.

Once the lipstick material has been added to the mixing container 54, the mixing container 54 is placed on a microwave safe dish and covered with a paper towel. The dish is then placed in a microwave oven and the oven is operated on a high setting for up 45 seconds (step 110). (Recommended time for a 1200 Watt oven.) After about 45 seconds, a towel or mitt is used to carefully remove the dish from the oven. If the lipstick mixture is not yet melted at this point, the material should be heated again for 15 seconds. This process is repeated until the lipstick mixture is melted thoroughly to the consistency of whole milk. The melted material should be stirred thoroughly and the color observed. Additional material may be added (and material may be removed) to adjust the color to obtain the desired results. If the consistency of the mixture is thinner than whole milk, it should be gently stirred for a few seconds and allowed to cool until it attains the proper consistency.

Once the lipstick mixture is the correct color and consistency, the mixture should immediately be poured into the mold 10 to fill it to the top of the upper section 36 (step 112). If lipstick material is leftover after the mold 10 has been filled, the extra material may be poured into the storage containers 60.

The filled lipstick mold 10 should be placed into a freezer on a flat surface for about ten minutes to allow the lipstick material to harden in the mold 10 (step 114). After about ten minutes, the lipstick mold 10 is removed from the freezer and is allowed to stand at room temperature for 30 minutes.

While the two lower mold halves 14a-14b are held together firmly, the upper mold section 30 is gently and slowly rotated about the mold axis until the upper mold section 30 snaps away from the lower mold halves 14a-14b (step 116). The upper mold section 30 is then carefully removed from the lower mold halves 14a-14b while they are continuously held firmly together (step 118). This exposes an upper portion of the molded stick of lipstick which extends from the lower mold halves 14a-14b.

With the cap removed from an empty lipstick applicator tube 52, the applicator tube outer shell should be twisted until the inside lipstick cup is extended all the way to the top. The empty lipstick applicator tube 52 is then turned upside down and the cup of the applicator tube is slowly pressed down onto the exposed lipstick material extending from the lower mold halves 14a-14b until the lipstick material is seated in the cup of the applicator tube 52 (step 120). The lipstick applicator tube 52 is then pulled gently and slowly upward to remove the newly-molded lipstick from the lower mold halves 14a-14b (step 122). If the newly molded lipstick does not lift out of the lower mold halves 14a-14b, the lower mold halves 14a-4b may be separated to expose the lipstick bullet. The lipstick applicator tube 52 is then twisted until the cup turns and gently removes the lipstick bullet from the lower mold half 14a-14b. The outer shell of the applicator tube 52 is now twisted until the cup is all the way down, and the cap is replaced.

Procedure for Using the Kit 50 to Mix Lip Gloss Products

Figure 6:
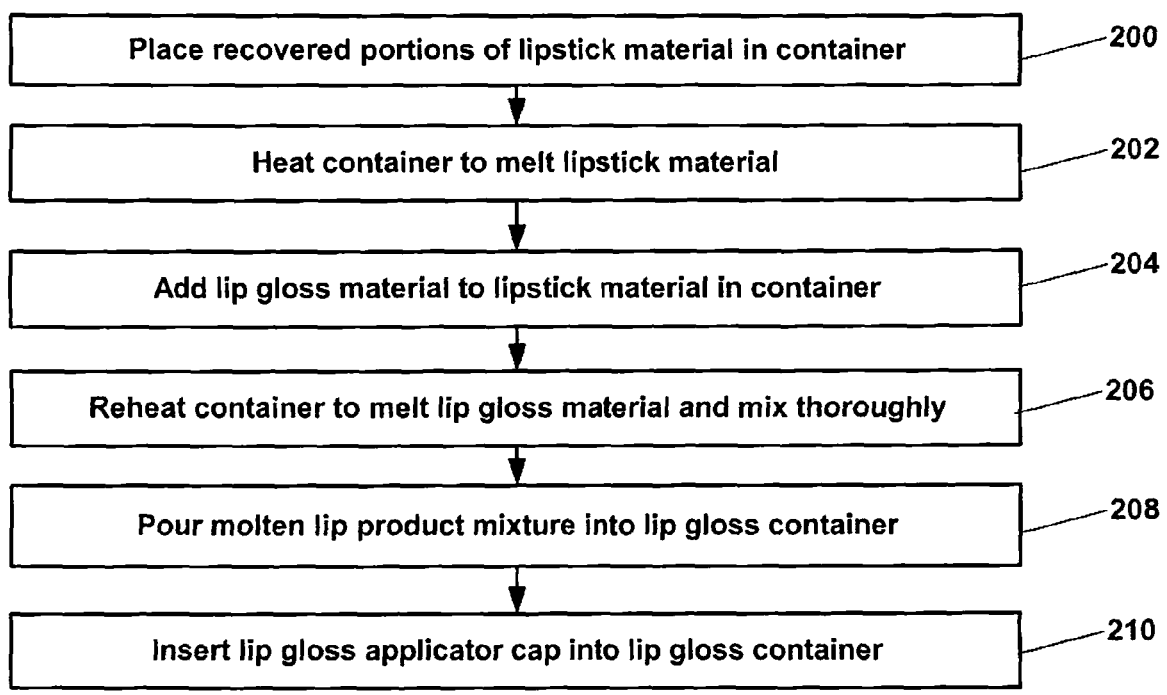
FIG. 6 depicts steps of a method for formulating lip gloss according to an embodiment of the invention

The kit 50 may also be used to mix lipstick materials of various colors with clear or colored lip gloss to create new lip gloss colors. The following procedure for mixing lip gloss is described with reference to the steps depicted in FIG. 6. Using the spatula 56, lipstick material is added to a mixing container 54 (step 200 of FIG. 6). Materials of different colors may be added to mix and obtain new colors. Once the lipstick material has been added to the mixing container 54, the mixing container 54 is placed on a microwave safe dish and covered with a paper towel. The dish is then placed in a microwave oven and the oven is operated on a high setting for up 45 seconds (step 202). (Recommended time for a 1200 Watt oven.) After about 45 seconds, a towel or mitt is used to carefully remove the dish from the oven. If the lipstick mixture is not yet melted at this point, the material should be heated again for 15 seconds. This process is repeated until the lipstick mixture is melted thoroughly to the consistency of whole milk. The melted material should be stirred thoroughly and the color observed. Additional material may be added (and material may be removed) to adjust the color to obtain the desired results. If the consistency of the mixture is thinner than whole milk, it should be gently stirred for a few seconds and allowed to cool until it attains the proper consistency.

Once the lipstick mixture is the desired color, clear or colored gloss material is added to the lipstick mixture (step 204) and the mixture is re-heated according to the instructions set forth above (step 206). Once the lip gloss mixture is the correct color and is the consistency of whole milk, the mixture should immediately be poured into a lip gloss container to the fill line (such as a six milliliter container) (step 208). If lip gloss material is leftover after the container has been filled, the extra material may be poured into a storage container 60. A wiper is then inserted into the opening of the lip gloss container and an applicator cap is inserted into the opening of the lip gloss container (step 210).

Although exemplary processes described herein preferably incorporate a microwave oven to generate heat for melting lipstick or lip gloss materials, those skilled in the art will appreciate that other types of ovens and heat sources may be used for this purpose. Thus, the invention is not limited to any particular oven or heat source for melting lipstick or lip gloss materials.

It will also be appreciated that that various additives may be incorporated into the lip product during the molding process, such as moisturizers, sunscreens, fragrances, flavors and frostings.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated.

The invention claimed is:

1. A mold for forming a stick of molded material, the mold comprising:
   a lower mold section having a lower mold cavity in which a lower portion of the stick of molded material is molded, wherein at least an upper portion of the lower mold cavity is substantially cylindrical and disposed along a central mold axis, the lower mold section comprising:
      a first lower mold portion in which a first half of the lower mold cavity is disposed; and
      a second lower mold portion in which a second half of the lower mold cavity is disposed;
   an upper mold section operable to engage the lower mold section, the upper mold section having a substantially cylindrical upper mold cavity disposed along the central mold axis in which an upper portion of the stick of molded material is molded, wherein the substantially cylindrical upper mold cavity engages the upper portion of the lower mold cavity to form a composite mold cavity when the upper mold section is engaged with the lower mold section, wherein the upper mold section is operable to rotate with respect to the lower mold section about the central mold axis when the upper mold section is engaged with the lower mold section; and
   means for causing the upper mold section to move away from the lower mold section due to rotation of the upper mold section about the central mold axis with respect to the lower mold section, thereby causing the upper mold cavity to separate from the lower mold cavity.

2. The mold of claim 1 wherein:
   the lower mold section includes a base section with an upper surface having one or more upwardly extending ramp members disposed thereon;
   the upper mold section includes one or more downwardly extending tabs that are in rotational alignment with the one or more ramp members of the lower mold section when the upper mold section is engaged with the lower mold section; and
   the means for causing the upper mold section to move away from the lower mold section comprises the one or more ramp members in sliding engagement with the one or more tabs as the upper mold section is rotated about the central mold axis with respect to the lower mold section 3. The mold of claim 1 wherein a lower portion of the lower mold cavity is bullet-shaped and has a flattened portion to one side.

4. The mold of claim 1 wherein the first and second lower mold portions include rib features on outer surfaces thereof which engage an inner surface of the upper mold section to align the upper mold cavity with the lower mold cavity along the central mold axis.

5. The mold of claim 1 wherein the upper mold section and the lower mold section include knurled outer surfaces which aid a user in gripping the surfaces and applying a rotational force thereto to rotate the upper mold section with respect to the lower mold section.

6. A kit for recovering portions of lip product and reformulating the recovered portions to form a stick of lip product, the kit comprising:
   one or more spatulas sized for recovering the portions of lip product from within used lip product applicator tubes;
   one or more containers for holding the recovered portions of lip product as the recovered portions are heated and melted;
   a mold for forming a stick of lip product from melted portions of lip product, the mold comprising:
      a lower mold section having a lower mold cavity in which a lower portion of the stick of molded material is molded, wherein at least an upper portion of the lower mold cavity is substantially cylindrical and disposed along a central mold axis, the lower mold section comprising:
         a first lower mold portion in which a first half of the lower mold cavity is disposed; and
         a second lower mold portion in which a second half of the lower mold cavity is disposed; and
      an upper mold section operable to engage the lower mold section, the upper mold section having a substantially cylindrical upper mold cavity disposed along the central mold axis in which an upper portion of the stick of molded material is molded, wherein the substantially cylindrical upper mold cavity engages the upper portion of the lower mold cavity to form a composite mold cavity when the upper mold section is engage with the lower mold section, wherein the upper mold section is operable to rotate with respect to the lower mold section about the central mold axis when the upper mold section is engaged with the lower mold section; and
      means for causing the upper mold section to move away from the lower mold section due to rotation of the upper mold section about the central mold axis with respect to the lower mold section, thereby causing the upper mold cavity to separate from the lower mold cavity; and
   one or more lip product applicator tubes, each for receiving a stick of lip product formed in the mold.

7. The kit of claim 6 further comprising one or more label stickers for applying to the one or more lip product applicator tubes.

8. The kit of claim 6 further comprising stackable storage containers for storing unused portions of lip product.

* * * * *